United States Patent
Kley et al.

(10) Patent No.: US 6,531,493 B1
(45) Date of Patent: Mar. 11, 2003

(54) 3-CYCLOPROPYLMETHOXY-4-DIFLUOROMETHOXY-N-(3,5-DICHLOROPYRID-4-YL)BENZAMIDE IN THE TREATMENT OF MULTIPLE SCLEROSIS

(75) Inventors: Hans-Peter Kley, Allensbach (DE); Karl Sanders, Konstanz (DE)

(73) Assignee: Altana Pharma AG, Konstanz (DE)

( * ) Notice: Subject to any disclaimer, the term of this patent is extended or adjusted under 35 U.S.C. 154(b) by 0 days.

(21) Appl. No.: 09/914,763

(22) PCT Filed: Mar. 1, 2000

(86) PCT No.: PCT/EP00/01703

§ 371 (c)(1),
(2), (4) Date: Sep. 5, 2001

(87) PCT Pub. No.: WO00/53182

PCT Pub. Date: Sep. 14, 2000

(30) Foreign Application Priority Data

Oct. 3, 1999 (EP) .............................. 99104793

(51) Int. Cl.[7] .............................................. A61K 31/44
(52) U.S. Cl. ...................................... 514/352; 514/903
(58) Field of Search ......................................... 514/352

(56) References Cited

FOREIGN PATENT DOCUMENTS

| WO | 94/02465 | 2/1994 |
|---|---|---|
| WO | 95/01338 | 1/1995 |
| WO | 95/28926 | 11/1995 |

OTHER PUBLICATIONS

Dinter, H., et al., "Phosphodiesterase type IV inhibitors in the treatment of multiple sclerosis". J. Mol. Med., 75:95–102 (1997).

Genain, Claude P., et al., "Prevention of autoimmune demyelination in non–human primates by a cAMP–specific phsophodiesterase inhibitor". Pro. Natl. Acad. Sci. USA, 92:3601–3605 (1995).

Navikas, V., et al., "The Phosphodiesterase IV Inhibitor Rolipram In Vitro Reduces the Numbers of MBP–Reactive IFN–γ and TNF–α MRNA Expressing Blood Mononuclear Cells in Patients with Multiple Sclerosis". Clinical Neuropharmacology, 21:236–244 (1998).

Sommer N., et al., "Therapeutic potential of phosphodiesterase type 4 inhibition in chronic autoimmune demyelinating disease", Journal of Neuroimmunology, 79:54–61 (1997).

*Primary Examiner*—Rebecca Cook
(74) *Attorney, Agent, or Firm*—Nath & Associates PLLC; Gary M. Nath; Todd L. Juneau

(57) ABSTRACT

The invention relates to the novel use of 3-cyclopropylmethoxy-4-difluoromethoxy-N-(3,5-dichloropyrid-4-yl)benzamide, a pharmacologically tolerable salt thereof or its N-oxide in the treatment of multiple sclerosis.

10 Claims, No Drawings

3-CYCLOPROPYLMETHOXY-4-DIFLUOROMETHOXY-N-(3,5-DICHLOROPYRID-4-YL)BENZAMIDE IN THE TREATMENT OF MULTIPLE SCLEROSIS

This is a 371 of PCT/EP00/01703 filed Mar. 1, 2000.

TECHNICAL FIELD

The invention relates to the novel use of 3-cyclopropylmethoxy4-difluoromethoxy-N-(3,5-dichloropyrid-4-yl)benzamide, a pharmacologically acceptable salt thereof or its N-oxide in the treatment of multiple sclerosis.

PRIOR ART

In the International Patent Application WO95/28926, PDE4 inhibitors—in particular rolipram—are proposed on their own or in combination with anti-inflammatory active compounds or immunomodulators for the treatment of multiple sclerosis. In the International Patent Application WO93/18770, tumor necrosis factor inhibitors—in particular pentoxyfylline—are proposed for the treatment of disorders of the central nervous system.

In the International Patent Application WO97/19686, the use of a combination of pentoxyfilline with type I interferons is described for the treatment of multiple sclerosis.

DESCRIPTION OF THE INVENTION

Multiple sclerosis is a degenerative disorder of the central nervous system, which is characterized by a localized disintegration of the myelin sheaths. The disorder proceeds chronically in episodes which are often far apart from one another in terms of time, often with regressions of the clinical symptomatology, but can also have a slow continuous progressive course.

The symptoms are varied, depending on the failure of the part of the nervous system affected in each case; for example, double images due to ophthalmoplegia, trembling, attacks of giddiness, myasthenia, incontinence, perception and speech disorders and psychological changes can occur.

The exact mechanism of development of multiple sclerosis is still not known. A possible cause discussed is, for example, a slow virus infection or an autoimmune disease.

With an incidence of approximately 5 to 100,000 inhabitants/year in Central Europe, multiple sclerosis is the most frequent neurological disorder. To date, the disorder can only be treated symptomatically by the high-dose administration of glucocorticoids on occurrence of acute episodes with neurological symptoms, which leads to a reduction in the duration of the episode. On account of the known, numerous and severe side effects of corticoids, however, it is not possible to carry out a preventive continuous therapy using these. Some patients also receive immunosuppressants; although these lower the episode rate they are often poorly tolerable. The administration of genetically engineered beta-interferons is relatively new and on regular injection they can lower the episode rate by approximately one third. The injection of beta-interferons, however, is difficult to handle for the patient and very cost-intensive.

It is therefore the object of the present invention to make available a preparation for the treatment of multiple sclerosis which overcomes the abovementioned disadvantages.

The object on which the invention is based is surprisingly achieved by the use of 3-cyclopropyl-methoxy-4-difluoromethoxy-N-(3,5-dichloropyrid-4-yl)benzamide, a pharmacologically tolerable salt thereof or its N-oxide in the treatment of the episodic or continuously progressive form of multiple sclerosis.

It has now been found that 3-cyclopropylmethoxy-4-difluoromethoxy-N-(3,5-dichloropyrid-4-yl)benzamide, a pharmacologically tolerable salt thereof or its N-oxide is also suitable, in addition to the previously mentioned indications, for the treatment of multiple sclerosis without the side effects often occurring with the abovementioned treatment methods appearing.

The invention thus relates in a first aspect to the use of 3-cyclopropylmethoxy-4-difluoromethoxy-N-(3,5-dichloropyrid-4-yl)benzamide, a pharmacologically tolerable salt thereof or its N-oxide in the production of medicaments for the treatment of multiple sclerosis, in particular of the episodically proceeding form of multiple sclerosis.

The invention further relates to the use of 3-cyclopropylmethoxy-4-difluoromethoxy-N-(3,5-dichloropyrid-4-yl)benzamide, a pharmacologically tolerable salt thereof or its N-oxide in the treatment of multiple sclerosis, in particular of the episodically proceeding form of multiple sclerosis.

The preparation of 3-cyclopropylmethoxy-4-difluoromethoxy-N-(3,5-dichloropyrid-4-yl)benzamide, its pharmacologically acceptable salts and its N-oxide [3-cyclopropylmethoxy-4-difluoromethoxy-N-(3,5-dichloro-1-oxypyrid-4-yl)benzamide] as well as the use of these compounds as phosphodiesterase (PDE) 4 inhibitors is described in WO95/01338.

In the use according to the invention of 3-cyclopropylmethoxy-4-difluoromethoxy-N-(3,5-dichloropyrid-4-yl)benzamide, a pharmacologically tolerable salt thereof or its N-oxide for the production of the abovementioned medicaments, 3-cyclopropylmethoxy-4-difluoromethoxy-N-(3,5-dichloropyrid-4-yl)benzamide, a pharmacologically tolerable salt thereof or its N-oxide are processed with suitable pharmaceutical excipients or vehicles to give tablets, coated tablets, capsules, suppositories, patches (e.g. as a transdermal therapeutic system=TTS), emulsions, suspensions or solutions, where the active compound content is advantageously between 0.1 and 95% and where, as a result of the appropriate choice of the excipients and vehicles, a pharmaceutical administration form exactly tailored to the active compound and/or to the desired onset of action (e.g. a sustained-release form or an enteric form) can be achieved.

The person skilled in the art is familiar on the basis of his expert knowledge with the excipients and vehicles which are suitable for the desired pharmaceutical formulations. In addition to solvents, gel-forming agents, suppository bases, tablet excipients and other active compound vehicles, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compound can be administered orally, rectally, parenterally or percutaneously.

In general, it has proven advantageous in human medicine to administer the active compound in the case of oral administration in a daily dose of approximately 0.05 to approximately 2 mg, in particular 0.1 to 1 mg, if appropriate in the form of a number, preferably 1 to 3, individual doses to achieve the desired result, where a gradually Increasing and reducing dose can be advantageous. In the case of parenteral treatment, it is possible to use similar or (in particular in the case of the intravenous administration of the active compound) as a rule lower doses.

It is known to the person skilled in the art that the optimum dose of an active compound can vary as a function of the body weight, the age and the general condition of the patient, and his/her response behavior to the active compound.

The optimum dose necessary in each case and manner of administration of the active compound can easily be fixed by any person skilled in the art on the basis of his expert knowledge.

If 3-cyclopropylmethoxy-4-difluoromethoxy-N-(3,5-dichloropyrid-4-yl)benzamide, a pharmacologically tolerable salt thereof or its N-oxide is to be employed for the treatment of multiple sclerosis, the pharmaceutical preparations can also contain one or more pharmacologically active constituents of other pharmaceutical groups.

Possible other pharmaceutical groups which may be mentioned are, for example, antiinflammatory active compounds, e.g. glucocorticosteroids such as methylprednisolone and prednisolone, ACTH, leukotriene antagonists, lipoxygenase inhibitors, immunosuppressants such as azothioprine, mixoribine, cyclosporin, gusperimus, tacrolimus, leflunomide, cyclophosphamide, methotrexate or mitoxantrone, immunomodulators such as type 1 interferons β 1a and 1b or 2a, linomide, aldesleukin, filgrastin, penicillamine, vinpocetine, pidotimod or imiquimod; furthermore cAMP-increasing substances, such as beta-mimetics, PGE2, PGI2, adenylate cyclase inhibitors, inhibitors of PDE1, PDE2, PDE3, PDE 4 and PDE7 and in particular inhibitors of the lymphocyte-specific PDE7A1; moreover inhibitors of a lymphocyte type 1 (Th1) population, mention being made here, for example, of cytokine antagonists against IL-1B, IL-2 and IL-12, TNFα and interferon γ, including antibodies, antisense oligonucleotides and soluble receptors; IL-10 agonists; inhibitors of lymphocyte activation, such as protein kinase C inhibitors, in particular against the PKC isoenzymes PKC-eta and PKC-theta, including antibodies and antisense oligonucleotides; furthermore inhibitors of the src–, itk- and MAP-kinases, inhibitors of the JAK1 and JAK2, inhibitors of STAT 4 and STAT 6, NFAT-, NF-kappa-B-, AP1- and SP1-antagonists, and inducers of T-cell apoptosis; in addition inhibitors of adhesion molecules and their ligands, which favor the migration of lymphocytes, such as alpha4β1-antagonists or VCAM-1-antagonists, and also metalloproteinase inhibitors.

A further subject of the invention is a commercially available product, consisting of a customary secondary pack, a primary pack containing the medicament (for example an ampoule or a blister pack) and, if desired, a pack insert, the medicament leading to the attenuation of the symptoms of multiple sclerosis, the suitability of the medicament for the treatment of multiple sclerosis being indicated on the secondary pack and/or on the pack insert of the commercially available product, and the medicament containing 3-cyclopropylmethoxy-4-difluoromethoxy-N-(3,5dichloropyrid-4-yl)benzamide, a pharmacologically tolerable salt therof or its N-oxide. The secondary pack, the primary pack containing the medicament and the pack insert otherwise correspond to what would be regarded as standard to the person skilled in the art for medicaments of this type.

Investigations Carried Out

Experimental autoimmune encephalomyelitis (EAE) is induced in a known manner (NAGELKERKEN et al, International Immunology, Vol. 9, No. 9, 1243–1251, 1997) in female SJL mice by administration of a proteolipid protein. The immunization is carried out with $PLP_{139-151}$ in Freund's complete adjuvant, which contains 1 mg of *Mycobacterium tuberculosis* H37Ra in one ml. 3 days later, $10^{10}$ heat-inactivated *Bordetella pertussis* organisms are administered intravenously. The administration of substance [2×5 mg/kg of 3-cyclopropylmethoxy-4-difluoromethoxy-N-(3,5-dichloropyrid-4-yl)benzamide (=substance A)] is carried out 2×daily, beginning on the day of EAE induction, continuously up to the 21st day after EAE induction. The clinical course of the animals is checked daily, assessed using a score system and compared with untreated controls.

TABLE 1

| Day after EAE induction | | Number of sick animals | | | | | | | | | | | |
|---|---|---|---|---|---|---|---|---|---|---|---|---|---|
| | n | 2 | 4 | 6 | 8 | 10 | 12 | 14 | 16 | 18 | 20 | 22 | 24 | 26 |
| Untreated control | 10 | 0 | 0 | 0 | 0 | 1 | 10 | 10 | 10 | 9 | 7 | 5 | 4 | 4 |
| 2 × 5 mg/kg (p.o.) of substance A | 10 | 0 | 0 | 0 | 0 | 0 | 0 | 1 | 3 | 3 | 3 | 3 | 4 | 3 |

As can be seen from Table 1, the oral administration of 3-cyclopropylmethoxy-4-difluoromethoxy-N-(3,5dichloropyrid-4-yl)benzamide leads on the one hand to a delay in the onset of the MS-analogous symptomatology and on the other hand to a marked decrease in the number of animals which suffer from the experimental encephalitis.

Whereas in the group of untreated experimental animals in the region of the 10th–12th day after EAE induction all experimental animals show disease symptoms, the first symptoms in the group treated with 3-cyclopropylmethoxy-4-difluoromethoxy-N-(3,5-dichloropyrid-4-yl)benzamide only occur in the region of the 14th–16th day after EAE induction. It is to be particularly emphasized in this connection that in the group of treated animals 6 of the 10 experimental animals showed no MS-analogous symptomatology at all in the monitoring period up to the 26th day after EAE induction.

The experimental results show that 3-cyclopropylmethoxy-4-difluoromethoxy-N-(3,5-dichloropyrid-4-yl)benzamide is suitable for the treatment of multiple sclerosis, in particular of the episodically proceeding form of multiple sclerosis.

What is claimed is:

1. A method for treating multiple sclerosis comprising the step of administering an effective amount of 3-cyclopropylmethoxy-4-difluoromethoxy-N-(3,5-dichloropyrid-4-yl)benzamide or its pharmaceutically acceptable salt to a patient in need thereof.

2. The method according to claim 1 wherein the multiple sclerosis is an episodically proceeding form of multiple sclerosis.

3. A method for treating multiple sclerosis comprising the step of administering an effective amount of 3-cyclopropylmethoxy-4-difluoromethoxy-N-(3,5-dichloro-1-oxipyrid-4-yl)benzamide to a patient in need thereof.

4. The method according to claim 3 wherein the multiple sclerosis is an episodically proceeding form of multiple sclerosis.

5. A method of treating multiple sclerosis comprising the steps of:

administering from about 0.05 mg to 2 mg of 3-cyclopropylmethoxy-4-difluoromethoxy-N-(3,5-dichloropyrid-4-yl)benzamide or its pharmaceutically acceptable salt to a patient in need thereof;

wherein said 3-cyclopropylmethoxy-4-difluoromethoxy-N-(3,5-dichloropyrid-4-yl)benzamide is administered in the form of a tablet, coated tablet or capsule.

6. The method according to claim 5 wherein the amount of said 3-cyclopropylmethoxy-4-difluoromethoxy-N-(3,5-dichloropyrid-4-yl)benzamide or its pharmaceutically acceptable salt administered is from about 0.1 mg to 1 mg.

7. The method according to claim 5 wherein the multiple sclerosis is an episodically proceeding form of multiple sclerosis.

8. A method of treating multiple sclerosis comprising the steps of:

administering from about 0.05 mg to 2 mg of 3-cyclopropylmethoxy-4-difluoromethoxy-N-(3,5-dichloro-1-oxipyrid-4-yl)benzamide to a patient in need thereof;

wherein said 3-cyclopropylmethoxy-4-difluoromethoxy-N-(3,5-dichloro-1-oxypyrid-4-yl)benzamide is administered in the form of a tablet, coated tablet or capsule.

9. The method according to claim 8 wherein the amount of said 3-cyclopropylmethoxy-4-difluoromethoxy-N-(3,5-dichloro-1-oxipyrid-4-yl)benzamide administered is from about 0.1 mg to 1 mg.

10. The method according to claim 8 wherein the multiple sclerosis is an episodically proceeding form of multiple sclerosis.

* * * * *